(12) United States Patent
Stucki et al.

(10) Patent No.: US 10,028,737 B2
(45) Date of Patent: Jul. 24, 2018

(54) PELVIC CABLE SOLUTION

(71) Applicant: DePuy Synthes Products, LLC, Raynham, MA (US)

(72) Inventors: Simon Stucki, Thun (CH); Guido Hertig, Burgdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 766 days.

(21) Appl. No.: 14/312,331

(22) Filed: Jun. 23, 2014

(65) Prior Publication Data
US 2014/0309690 A1 Oct. 16, 2014

Related U.S. Application Data

(63) Continuation of application No. 12/863,858, filed as application No. PCT/US2009/033404 on Feb. 6, 2009, now Pat. No. 8,795,343.
(Continued)

(51) Int. Cl.
*A61B 17/04* (2006.01)
*A61B 17/88* (2006.01)
(Continued)

(52) U.S. Cl.
CPC ...... *A61B 17/0487* (2013.01); *A61B 17/8869* (2013.01); *A61B 17/8066* (2013.01); *A61B 17/842* (2013.01)

(58) Field of Classification Search
CPC ..... A61B 17/808; A61B 17/82; A61B 17/842; A61B 17/8861; A61B 17/8869; A61B 17/8872
See application file for complete search history.

(56) References Cited

U.S. PATENT DOCUMENTS 630,428 A 8/1899 Wahlert
904,341 A 11/1908 Lindstrom
(Continued)

FOREIGN PATENT DOCUMENTS

CA 2234782 10/1998
CN 1819800 4/2010
(Continued)

*Primary Examiner* — Nicholas Woodall
(74) *Attorney, Agent, or Firm* — Fay Kaplun & Marcin, LLP

(57) ABSTRACT

A device for treating bone fractures, comprises an actuating mechanism removably coupleable to a clamping mechanism including a clamp defining a cable receiving channel extending therethrough and a compression member coupled to the clamp for movement relative thereto, movement of the compression member relative to the clamp in a first direction moving the clamping mechanism into a clamping configuration in which at least a portion of the clamp is compressed into the channel to fix a cable received therein relative to the clamping mechanism. The actuating mechanism includes a first member and a second member removably engagable with a clamping mechanism so that, when engaged, relative movement between the first and second members causes relative movement between the clamp and the compression member to move the clamping member between the clamping configuration and a release configuration, the actuating mechanism further including a tensioning mechanism.

6 Claims, 16 Drawing Sheets

Related U.S. Application Data

(60) Provisional application No. 61/026,807, filed on Feb. 7, 2008.

(51) Int. Cl.
*A61B 17/84* (2006.01)
*A61B 17/82* (2006.01)
*A61B 17/80* (2006.01)

(56) References Cited

U.S. PATENT DOCUMENTS

| | | | |
|---|---|---|---|
| 2,049,361 A * | 7/1936 | Ericsson | A61B 17/8861 |
| | | | 100/32 |
| 2,755,110 A | 7/1956 | Jacobs | |
| 2,943,650 A * | 7/1960 | Rubin | A61B 17/8861 |
| | | | 140/119 |
| 3,361,460 A | 1/1968 | Jansen | |
| 3,923,406 A | 12/1975 | Iritz | |
| 4,095,914 A | 6/1978 | Thomsen | |
| 4,454,876 A | 6/1984 | Mears | |
| 4,573,458 A | 3/1986 | Lower | |
| 4,848,953 A | 7/1989 | Young | |
| 4,893,846 A | 1/1990 | Mcgraw | |
| 5,145,186 A | 9/1992 | Maleski | |
| 5,312,410 A | 5/1994 | Miller et al. | |
| 5,449,361 A * | 9/1995 | Preissman | A61B 17/82 |
| | | | 140/123.5 |
| 5,536,270 A | 7/1996 | Songer et al. | |
| 5,649,927 A | 7/1997 | Kilpela et al. | |
| 5,702,397 A * | 12/1997 | Goble | A61B 17/0401 |
| | | | 606/232 |
| 5,782,831 A | 7/1998 | Sherman et al. | |
| 5,908,421 A * | 6/1999 | Beger | A61B 17/82 |
| | | | 606/151 |
| 6,398,787 B1 | 6/2002 | Itoman | |
| 6,436,099 B1 | 8/2002 | Drewry et al. | |
| 6,488,317 B1 | 12/2002 | Daoud | |
| 7,172,595 B1 * | 2/2007 | Goble | A61B 17/1714 |
| | | | 606/86 A |
| 8,241,288 B2 * | 8/2012 | Justin | A61B 17/82 |
| | | | 606/74 |
| 8,267,974 B2 | 9/2012 | Schlafli et al. | |
| 8,795,343 B2 * | 8/2014 | Stucki | A61B 17/8869 |
| | | | 606/103 |
| 2002/0042654 A1 | 4/2002 | Masini | |
| 2002/0128653 A1 | 9/2002 | Haidukewych | |
| 2003/0083669 A1 * | 5/2003 | Gleason | A61B 17/8861 |
| | | | 606/103 |
| 2005/0165401 A1 | 7/2005 | Pack | |
| 2006/0135958 A1 | 6/2006 | Marissen et al. | |
| 2009/0171357 A1 | 7/2009 | Justin et al. | |

FOREIGN PATENT DOCUMENTS

| | | |
|---|---|---|
| EP | 0105655 A1 | 4/1984 |
| FR | 2631539 A1 | 11/1989 |
| GB | 272613 A | 6/1927 |
| GB | 587076 A | 4/1947 |
| GB | 667287 A | 2/1952 |
| GB | 713956 A | 8/1954 |
| GB | 778929 A | 7/1957 |
| GB | 812569 A | 4/1959 |
| GB | 874643 A | 8/1961 |
| GB | 959137 A | 5/1964 |
| GB | 968612 A | 9/1964 |
| GB | 987717 A | 3/1965 |
| GB | 1021679 A | 3/1966 |
| GB | 1172097 A | 11/1969 |
| GB | 1331507 A | 9/1973 |
| GB | 2031731 A | 4/1980 |
| GB | 2069170 A | 8/1981 |
| GB | 2281948 A | 3/1995 |
| UA | 71829 A | 12/2004 |
| WO | 2000064363 A2 | 11/2000 |
| WO | 2001091660 A1 | 12/2001 |
| WO | 2002038059 A2 | 5/2002 |
| WO | 2006094749 A1 | 9/2006 |

* cited by examiner

PELVIC CABLE SOLUTION

PRIORITY CLAIM

The present application is a Continuation Application of pending U.S. patent application Ser. No. 14/312,331 filed on Jun. 23, 2014; which is a Continuation Application of U.S. patent application Ser. No. 12/863,858 filed on Jul. 21, 2010, now U.S. Pat. No. 8,795,343; which is 371 of PCT Application. Ser. No. PCT/US2009/033404 filed on Feb. 6, 2009, which claims priority to U.S. Provisional Application Ser. No. 61/026,807 filed on Feb. 7, 2008. The disclosure of the above patent(s)/application(s) is incorporated herein by reference.

BACKGROUND

Acetabular (hip socket) fractures are serious orthopedic injuries usually resulting from significant trauma. Surgery to realign and stabilize the displaced joint surfaces (e.g., using plates and screws), allows the patient to avoid traction and prolonged bedrest and accurate fracture realignment promotes improved bone and cartilage healing, which in turn improves long-term results. Early fracture stability allows comfortable hip movement which improves joint cartilage healing. Additionally, this allows patients to be out of bed and ambulatory.

However, acetabular fractures with medial displacement patterns, particularly those with medial displacement of the quadrilateral surface, may be technically challenging to treat. The location of the affected area deep in the pelvic part of the abdominal cavity, minimal bone stock and difficulty obtaining stable internal fixation in the true pelvis contribute to the surgical challenge of open reduction and internal fixation of such fractures. Applying a medial buttress plate across the quadrilateral surface may assist in preventing the femur head from penetrating into the pelvic cavity. However, because of the limited access to the quadrilateral surface and the thin bone structures around the acetabulum, it is often difficult to treat such fractures with standard plates and screws. Although procedures have previously been described for treating quadrilateral surface fractures, there is still no optimal mechanical solution. Most of the techniques involve fixations with forces acting at 90° to a screw axis, which may, when bone thickness is limited, result in a cut out of the screws.

SUMMARY OF THE INVENTION

The present invention is directed to a device for treating bone fractures, comprising an actuating mechanism removably coupleable to a clamping mechanism including a clamp defining a cable receiving channel extending therethrough and a compression member coupled to the clamp for movement relative thereto, movement of the compression member relative to the clamp in a first direction moving the clamping mechanism into a clamping configuration in which at least a portion of the clamp is compressed into the channel to fix a cable received therein relative to the clamping mechanism. The actuating mechanism includes a first member removably engagable with a clamping mechanism so that, when engaged, the first member prevents relative movement between the clamp and the first member, a second member removably engagable with a clamping mechanism and movably coupled to the first member so that, when engaged, the second member prevents relative movement between the compression member and the second member, relative movement between the first and second members causing relative movement between the clamp and the compression member to move the clamping member between the clamping configuration and a release configuration in which the cable is permitted to move through the clamping mechanism and a tensioning mechanism for drawing the cable through the clamping mechanism and applying a desired degree of tension thereto.

BRIEF DESCRIPTION OF THE DRAWINGS

FIG. 5b shows a front plan view of the clamp of FIG. 5a;

FIG. 6b shows a front plan view of the clamping ring of FIG. 6a;

DETAILED DESCRIPTION

Figure 1:
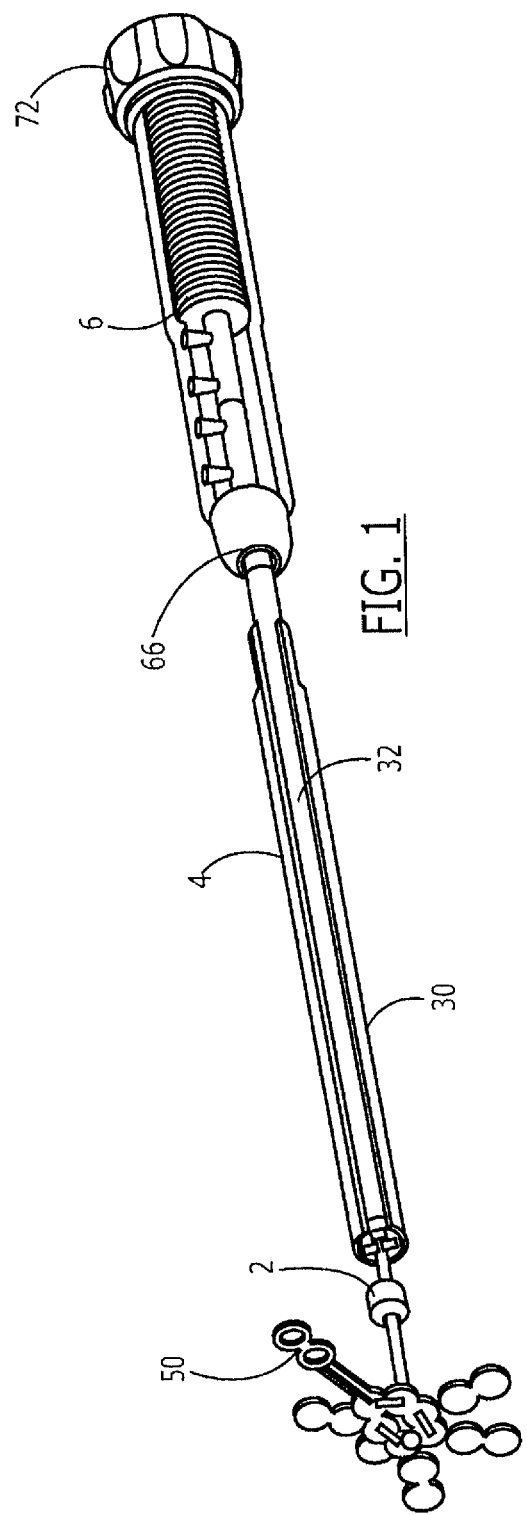
FIG. 1 shows a system of an exemplary embodiment of the present invention, with all its components fully assembled.

The present invention, which may be further understood with reference to the following description and the appended drawings, relates to a system and method for treating fractures, and in particular relates to internal fixation devices for treating fractures. Specifically, exemplary embodiments of the present invention describe a system and method for securing a cable or wire through the fractured quadrilateral surface of the acetabulum. It should be noted however, that although the embodiments of the present invention are described in regard to the application of a buttress plate to the quadrilateral surface of the acetabulum using surgical cable or wire, the present invention is relevant to the use of cable or wire to secure any bone fixation device to any bone.

As shown in FIGS. 1-6, a system according to an exemplary embodiment of the present invention includes a handle 6 for tensioning a cable 56 and a longitudinal member 4 for operating a clamping mechanism 2 to secure a clamp 8 about the cable 56 fixing the cable 56 at a desired location and tension as will be described in more detail below. The longitudinal member 4 is coupled to the handle 6 so that the cable 56 may be passed into the longitudinal member 4 and therethrough into the handle 6. As will be described in more detail below, the cable 56 is first inserted through and coupled to a bone plate 50 passed through a fractured bone and then fed through a clamping mechanism 2 into the longitudinal member 4 and from there into the handle 6. The longitudinal member 4 engages the clamping mechanism 2 which includes a clamping ring 10 screwed over a threaded, proximal end of a clamp 8 such that rotation of the longitudinal member 4 rotates the clamping ring 10 over the clamp 8, crushing the clamp 8 and securing it over the cable 56 maintaining a position of the clamp 8 on the cable 56. Thus, any tension on the cable 56 at this point is maintained by the clamp 8 securing the bone plate 50 against the fractured bone.

Figure 2:
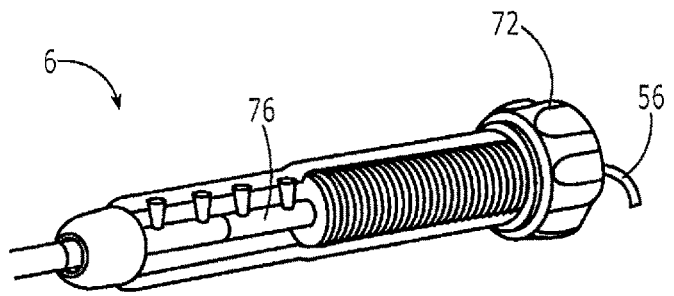
FIG. 2 shows a perspective view of a handle of an exemplary system of the present invention.

As shown in FIG. 2, the handle 6 is preferably longitudinally shaped to facilitate handling by a user with a channel 76 extending therethrough for slidably receiving the cable 56. However, those skilled in the art will understand that the shape of the handle is not critical to the invention and may be any selected shape. The channel 76 extends to a tensioning mechanism operated by a knob 72 formed, for example, at a proximal end of the handle 6. As would be understood by those skilled in the art, the tensioning mechanism may, for example, include a spool coupled to the knob 72. The cable 56 is coupled to the spool and a ratchet mechanism (or other suitable device) maintains tension on the cable 56 as the cable 56 is wound up on the spool by rotation of the knob 72. As would be understood by those skilled in the art, the tensioning mechanism may further include a manual release disengaging the ratchet mechanism to release tension from the cable 56 as desired. The handle 6 may further include an indicator or scale allowing a user to determine a current level of tension on the cable 56. A distal end 66 of the handle 6 is adapted to be coupled to the longitudinal member 4 as will be described in more detail below. In an exemplary embodiment, the distal end 66 may includes a recess adapted to receive a complimentarily shaped proximal end of an inner sleeve 32 of the longitudinal member 4 to prevent rotation of the end of internal sleeve 32 relative to the handle 6.

Figure 3:
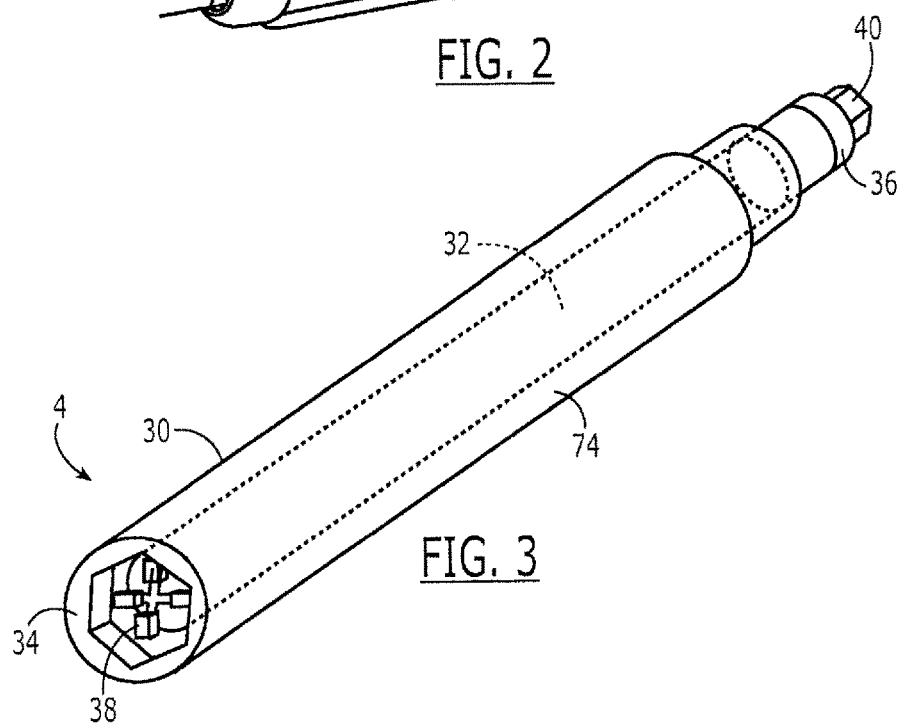
FIG. 3 shows a perspective view of longitudinal member of an exemplary system of the present invention.
Figure 4A:
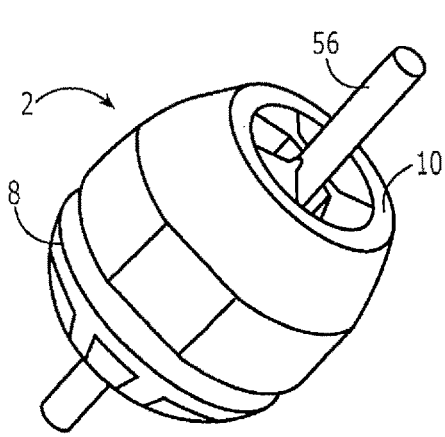
FIG. 4a shows a perspective view of a clamping mechanism according to an exemplary system of the present invention.
Figure 4B:
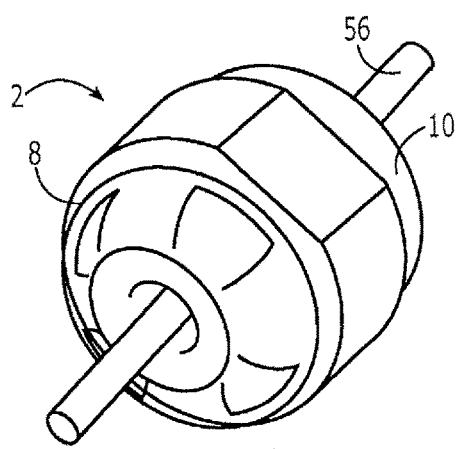
FIG. 4b shows a first perspective view of a clamping mechanism according to an exemplary system of the present invention.

As shown in FIG. 3 and mentioned above, the longitudinal member 4 comprises an outer sleeve 30 and an inner sleeve 32 rotatably housed therewithin. A distal end of the outer sleeve 30 includes a recess 34 shaped to engage a proximal end of the clamping ring 10 preventing the clamping ring 10 from rotating relative thereto. In a preferred embodiment, for example, the recess 34 and the proximal end of the clamping ring 10 are hexagonally shaped. However, those skilled in the art will understand that any of a variety of shapes may be selected for the clamping ring 10 and the recess 34 so long as the two elements are non-rotatable relative to one another when coupled together. A proximal end 36 of the outer sleeve 30 may be shaped to facilitate engagement with a wrench, or other tool for applying torque thereto to rotate the outer sleeve 30 about a longitudinal axis thereof while the handle 6 is held stationary. A distal end 38 of the inner sleeve 32 includes a mating feature sized and shaped to non-rotatably engage a proximal end of the clamp 8 (e.g., via a hole in the proximal end of the clamping ring 10). Thus, the rotation of the outer sleeve 30 relative to the handle 6 and, consequently, the inner sleeve 32, causes the clamping ring 10 to rotate relative to the clamp 8, screwing the clamping ring 10 over the clamp 8. In a preferred embodiment the distal end 38 may be crown-shaped. As indicated above, a proximal end 40 of the inner sleeve 32 extends through the outer sleeve 30 to non-rotatably engage a distal end 66 of the handle 6 with a channel 74 extending through the inner sleeve 32 being in communication with the channel 76 of the handle 6. Thus, as shown in FIGS. 4a and 4b, the cable 56 may pass through the longitudinal member 4 via channel 74 into the handle 6 and pass therethrough to the tensioning mechanism via the cannel 76. In an exemplary embodiment, the proximal end 40 may be hexagonally shaped to be received within a hexagonal recess of the distal end 66 of the handle 6.

Figure 5A:
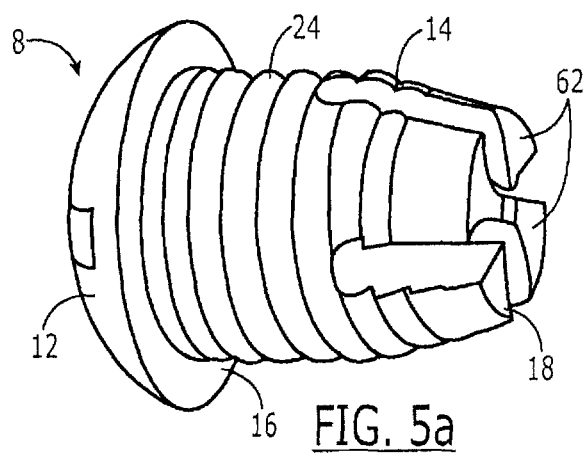
FIG. 5a shows a second perspective view of a clamp according to an exemplary embodiment of a system according to the present invention.
Figure 5B:
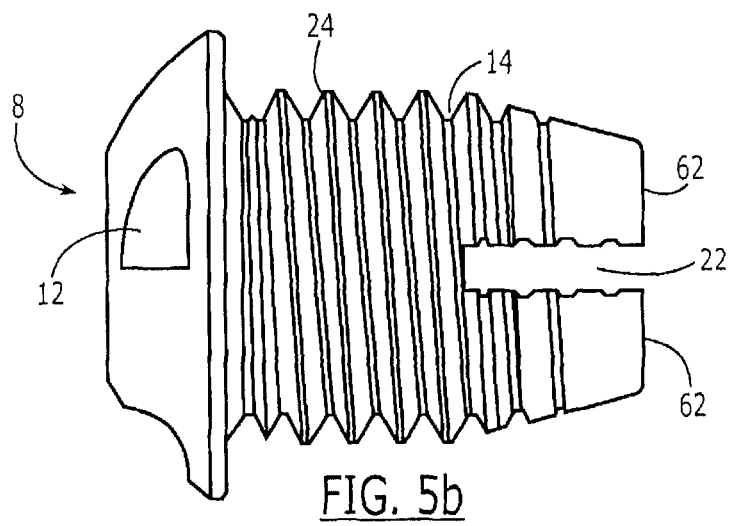
Figure 6A:
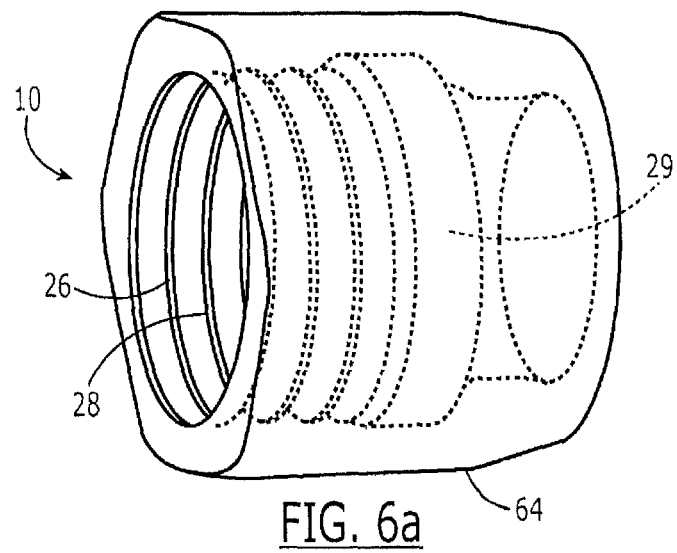
FIG. 6a shows a perspective view of a clamping ring according to an exemplary embodiment of a system of the present invention.
Figure 6B:
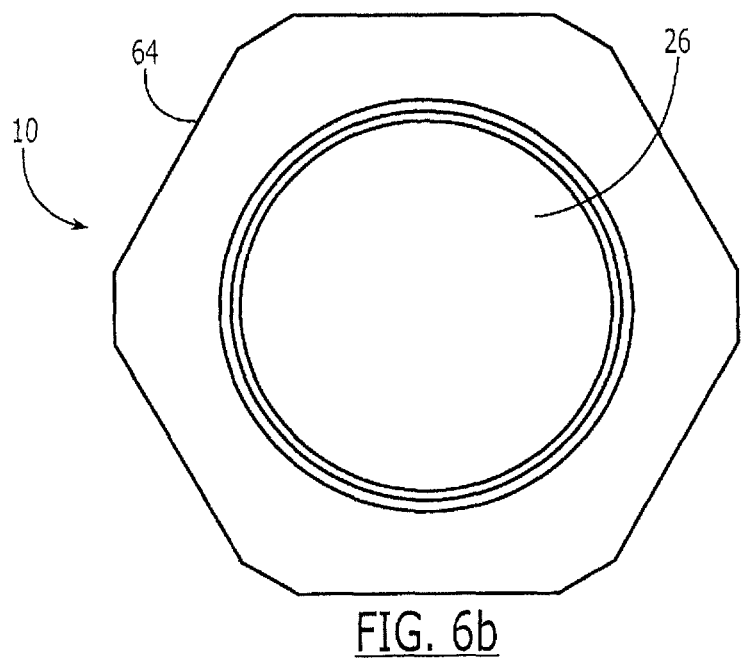

As shown in FIGS. 5a and 5b, the clamp 8 includes a head 12 and a body 14 extending proximally from the head 12 to a proximal end 18. The head 12 of the clamp 8 may be spherically shaped to adapt to the bone surface. However, it will be understood by those of skill in the art that the head 12 may be of a variety of shapes. The body 14 may be tapered with a diameter of a distal end 16 thereof slightly greater than that of the proximal end 18. The clamp 8 may further include a channel 20 extending therethrough so that the cable 56 may pass through the entire length of the clamp 8. The channel 20 may be substantially cylindrical and extend along a longitudinal axis of the clamp 8. Alternatively, the channel 20 may taper with the shape of the body 14. The body 14 may include threading 24 along all or a portion of its length and includes at least one slot 22 extending substantially longitudinally therethrough from the proximal end 18 toward the distal end 16. The longitudinal slots 22 may be parallel to the longitudinal axis of the clamp 8 along at least a portion of a length of the body 14 at its proximal end 18. The longitudinal slots 22 may, for example, be positioned substantially symmetrically about the longitudinal axis such that separated portions 62 of the proximal end 18 created by the longitudinal slots 22 are free to flex radially into the channel 20 against the cable 56. For example, in an exemplary embodiment, two longitudinal slots 22 substantially orthogonal to one another divide the proximal end 18 of the body 14 into four substantially equally sized and spaced portions 62.

Figure 7A:
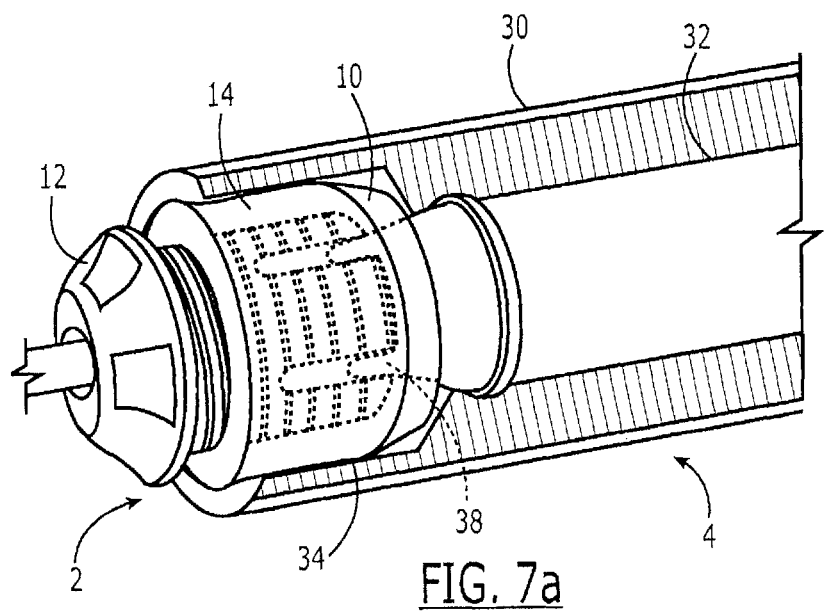
FIG. 7a shows a first perspective view of a longitudinal member assembled with a clamping mechanism according to an exemplary embodiment of a system of the present invention.
Figure 7B:
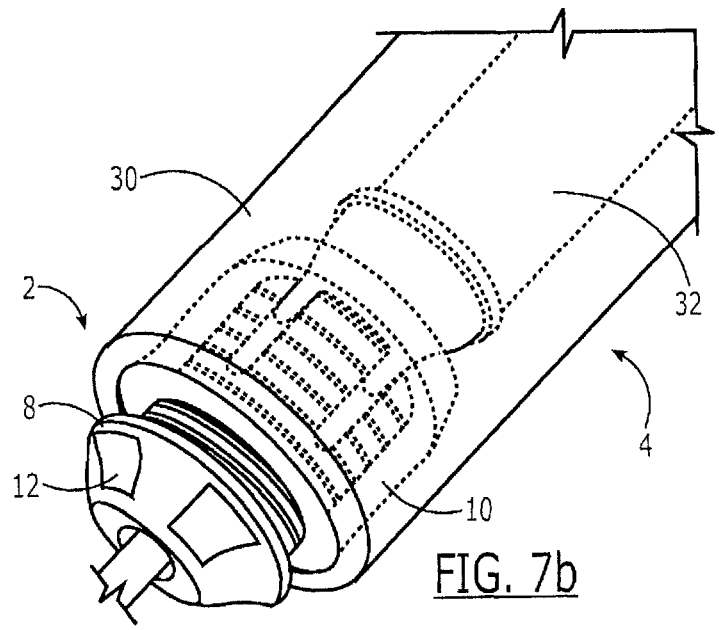
FIG. 7b shows a second perspective view of a longitudinal member engaging a clamping mechanism according to an exemplary embodiment of a system of the present invention.
Figure 7C:
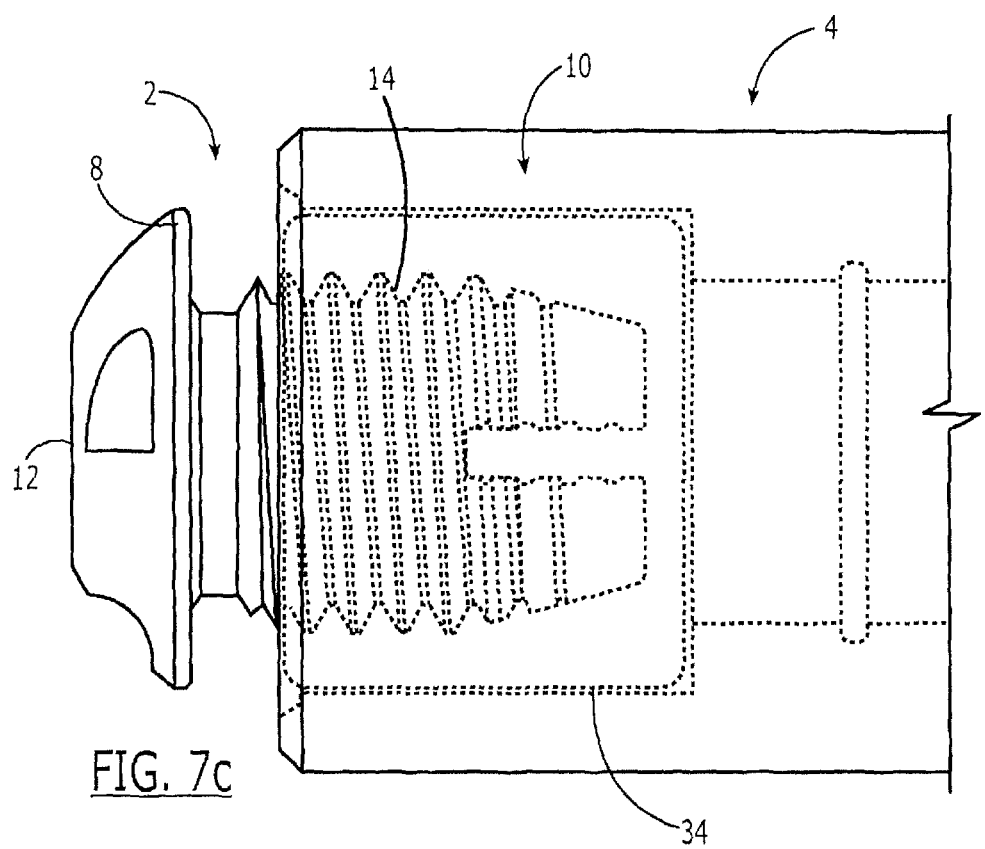
FIG. 7c shows a third perspective view of a longitudinal member engaging a clamping mechanism according to an exemplary embodiment of a system of the present invention.

As indicated above, the body 14 is threaded to engage a threading of a channel 26 of extending through a clamping ring 10 formed, for example, as a nut. A distal end of the channel 26 is sized and shaped to receive larger distal end 16 of the body 14 while a chamfer 29 necks down a proximal portion of the channel 26 so that, as the clamping ring 10 is threaded further distally over the body 14, the reduced diameter proximal portion of the channel 26 engages the portions 62 of the clamp 8 and forces them radially into the channel 20 against the cable 56. In a preferred embodiment, an outer surface 64 of the clamping ring 10 is hexagonally shaped to engage a corresponding recess 34 in the outer sleeve 30 as shown in FIGS. 7a-7c. It will be understood by those in the art however, that the outer surface 64 of the clamping ring 10 may take any shape so long as the outer surface 64 of the clamping ring 10 is non-rotatably engaged by the outer sleeve 30. As the clamping ring 10 is rotated relative to the clamp 8, the threads 28 engage the threads 24 of the clamp 8 to draw the clamping ring 10 distally relative to the body 14 compressing the portions 62 against the cable 56. Furthermore, as indicated above, the distal end 38 of the inner sleeve 32 engages the longitudinal slots 22 or any other feature of the clamp 8 to non-rotatably couple thereto. For example, in a preferred embodiment, the distal end 38 include projections (e.g., in the shape of an X or a cross) to extend into the longitudinal slots 22 to prevent relative rotation between the inner sleeve 32 and the clamp 8.

Figure 8:
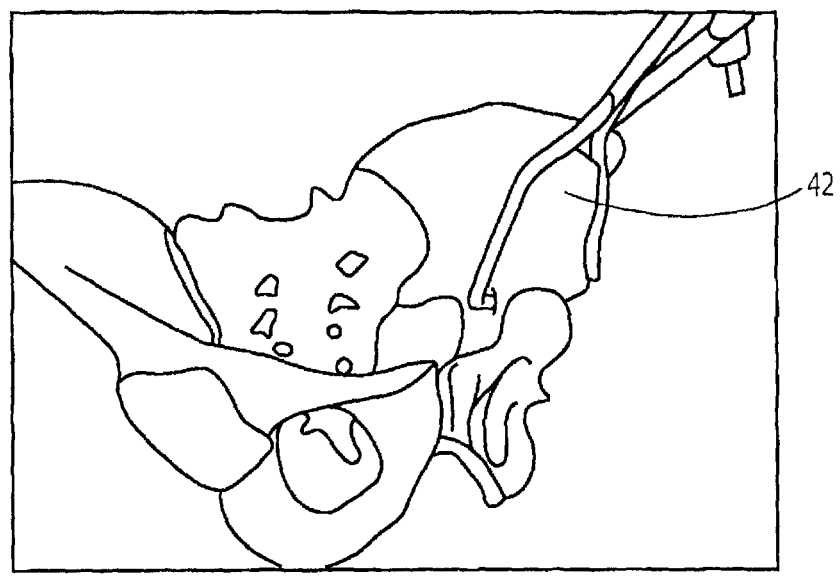
FIG. 8 shows an anatomically repositioning a fractured bone, according to an exemplary embodiment of a method of the present invention.
Figure 9:
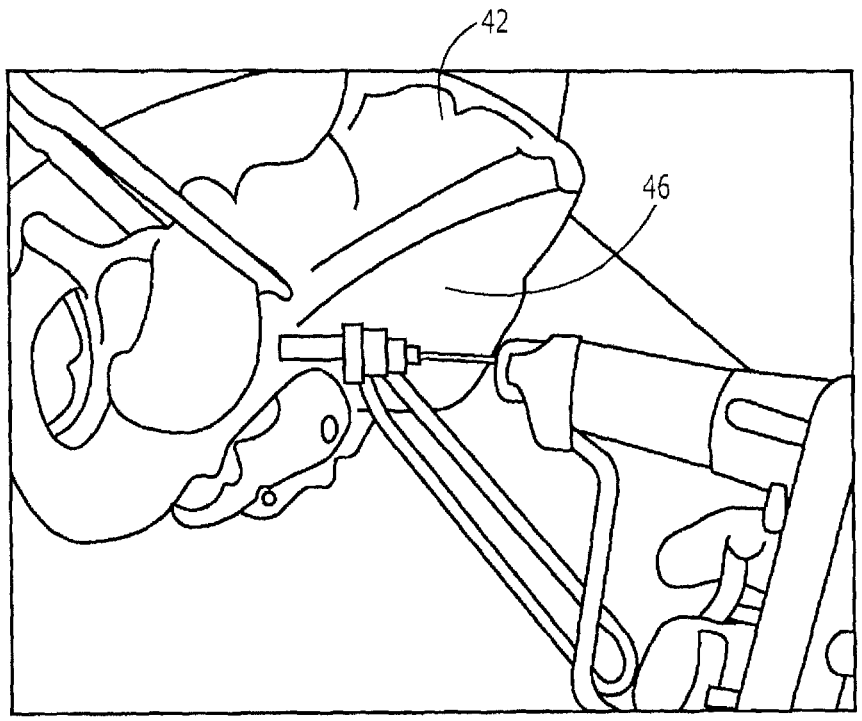
FIG. 9 shows the insertion of a cable (e.g., a Kirschner wire) from a dorso-lateral side of a pelvic bone through the repositioned quadrilateral surface of a bone fragment, according to an exemplary embodiment of the present invention.
Figure 10:
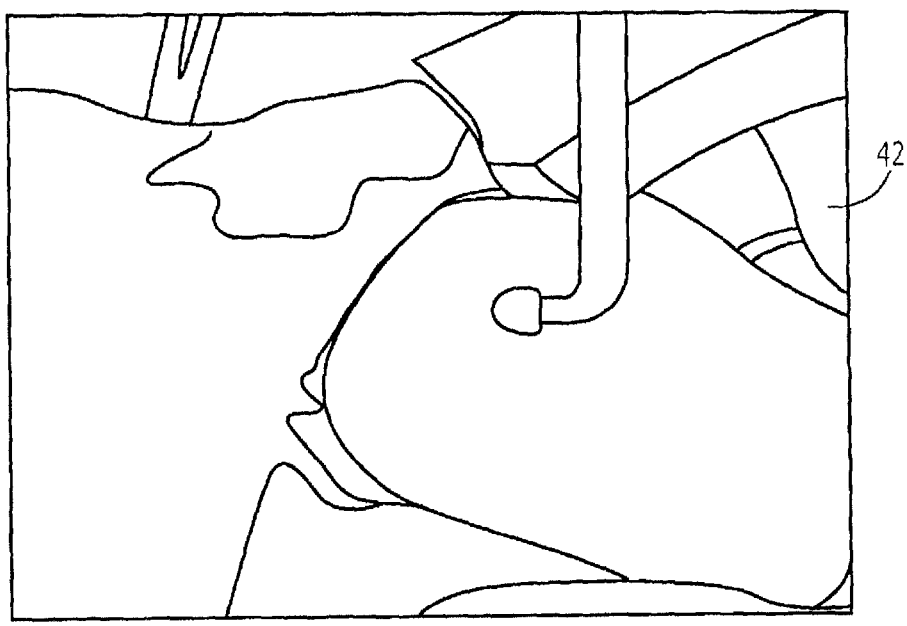
FIG. 10 shows holding a repositioned bone fragment, according to an exemplary embodiment of the present invention.
Figure 11:
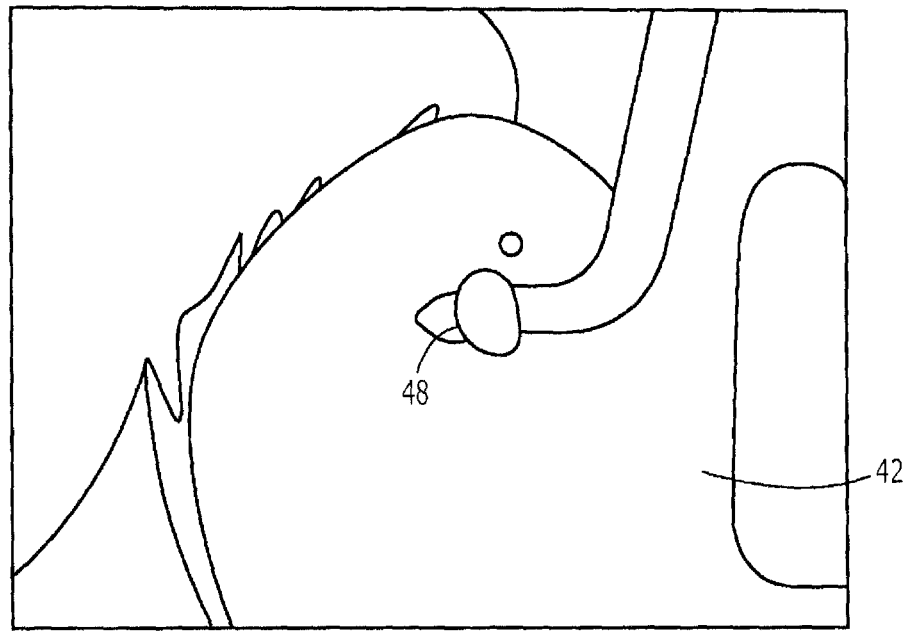
FIG. 11 shows drilling a hole through the fractured bone, according to an exemplary embodiment of the present invention.

As shown in FIGS. 8-21, a method according to an exemplary embodiment of the present invention provides improved mechanical buttressing of a fractured pelvis by fixing a plate over the quadrilateral surface of the acetabulum via a cable 56 and clamp 8 as described above. As shown in FIG. 8, to prepare for the surgical reduction of the fracture, the fractured bone 42 is anatomically repositioned (e.g., using clamps, forceps or any other surgical tool for holding the fractured bone 42 in place) and held in place as a wire is fixed to a target location on a dorso-lateral side 46 of the bone 42, as shown in FIG. 9. Those skilled in the art will understand that the wire may be any thin wire that can act as a guidewire for surgical tools such as, a K-wire, which is a sterilized, sharpened, smooth stainless steel pin that may be driven into the bone using a power or hand drill. The wire may be inserted into the bone 42 until an end is within the center of a target area of the quadrilateral surface of the bone 42, as shown in FIG. 10. A cannulated drill bit may then be mounted over the wire so that the wire functions as a guidewire aiming the drill to create a channel 48 through the quadrilateral surface, as shown in FIG. 11. Once the channel 48 has been drilled through the bone, the wire is removed from the body, while a physician continues to hold the fractured bone 42 in place.

Figure 12:
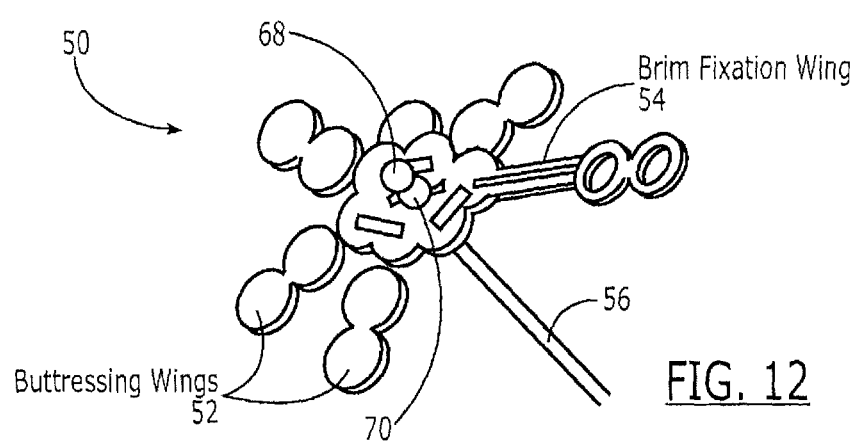
FIG. 12 shows assembling a component of an exemplary system, according to an exemplary embodiment of the present invention.

As shown in FIG. 12, a plate 50 may be pre-assembled for implantation into the body. The plate 50 may be selected according to the type of fracture of the bone and the support required to reduce the fracture. For example, the plate 50 may include one or more buttressing wings 52 and a brim fixation wing 54. The buttressing wings 52 may be pre-bent to adapt to the curve and shape of the quadrilateral surface. Additionally, the brim fixation wing 54 may be pre-bent to fit the curve if the pelvic brim. Alternatively, a user of the plate 50 may shape the plate 50 as desired to accommodate the anatomy of the target area as would be understood by those skilled in the art. Thus, the plate 50 is preferably formed of a material sufficiently strong to withstand the forces to which it will be exposed when implanted but which is sufficiently flexible to adapt to the shape of the bone 42 and to receive any bending required by a user. The plate 50 may be assembled with a cable 56 inserted through a hole 58 formed, for example, at or near a center thereof so that tension applied to the cable 56 draws the entire plate 50 snugly against the bone 42. The cable 56 may be fixed to the plate 50 by any known mechanism (e.g., by an enlarged distal end 68 sized to prevent the cable 56 from slipping through the plate 50). Thus, if the end 68 is rounded, a diameter of the rounded end 68 is selected to be greater than the diameter of the hole 58. The plate 50 may further include an indentation 70, or cavity, to accommodate the end 68 of the cable 56. It will be understood by those of skill in the art that the plate 50 need not be pre-assembled prior to implantation and that the cable 56 may be inserted through the hole 58 after the plate 50 has been positioned on the quadrilateral surface.

Figure 13:
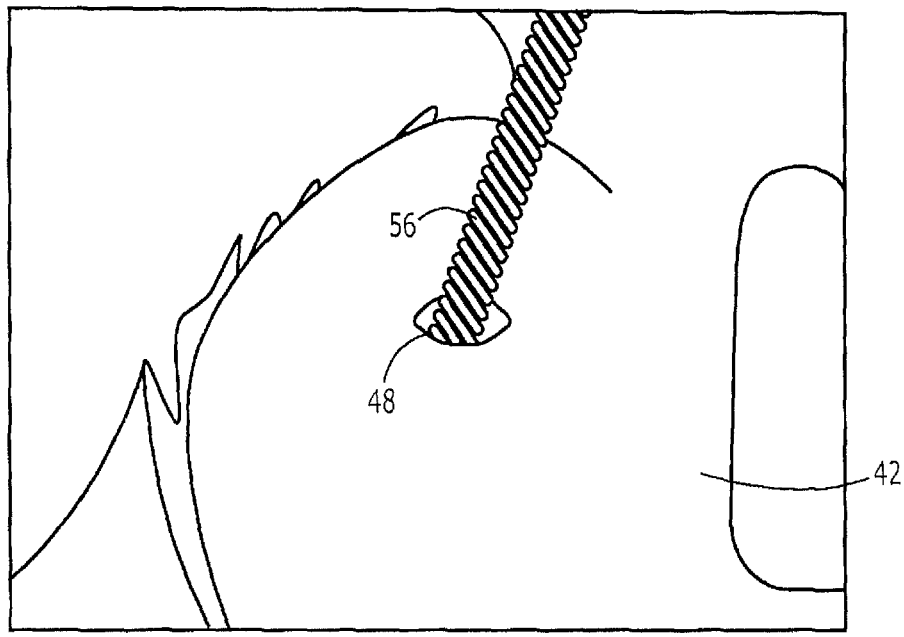
FIG. 13 shows inserting a cable into the drilled hole in the fractured bone, according to an exemplary embodiment of the present invention.
Figure 14:
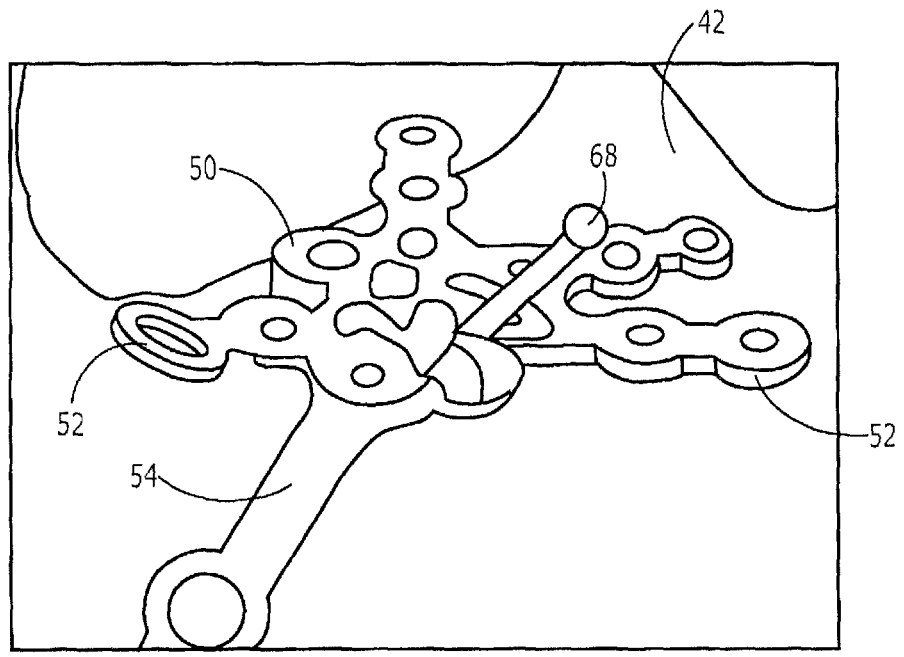
FIG. 14 shows the buttress plate abutting the surface of the bone, according to an exemplary embodiment of the present invention.

As shown in FIGS. 13-14, the proximal end of the cable 56 is passed through the channel 48 to the dorso-lateral side 46 of the bone 42 and pulled proximally until the plate 50 is held against the quadrilateral surface supporting the fractured bone 42, as shown in FIG. 14. Once the cable 56 is pulled taught, the cable 56 will extend at an angle that is approximately 45° relative to a plane in which the plate 50 rests, minimizing the likelihood of cut-out of the bone while continuing to sufficient support to stabilize the fragments of the bone 42 in the desired position. The plate 50 is preferably positioned such the buttressing wings 52 optimally buttress the quadrilateral surface and so that the fixation wing 54 fits over the pelvic brim.

Figure 15:
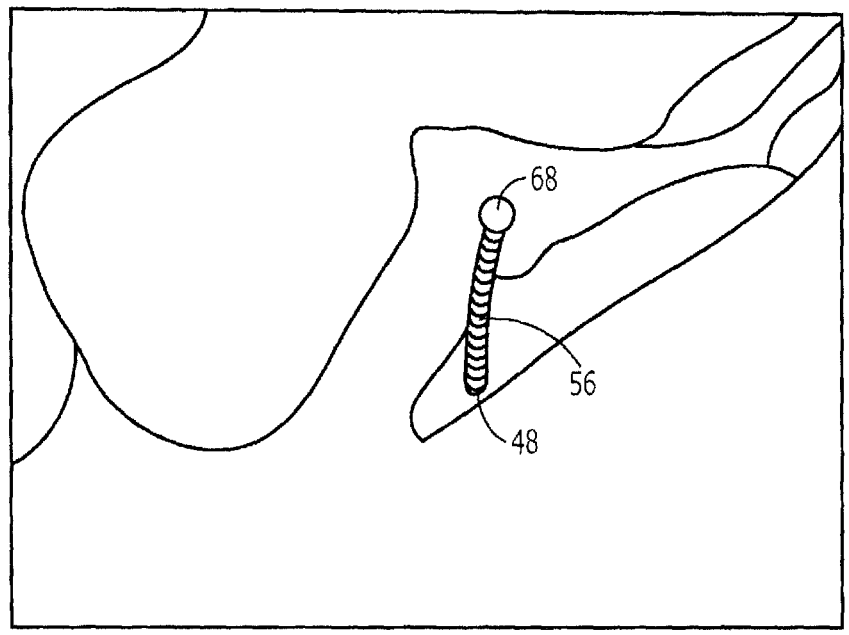
FIG. 15 shows inserting a cable into the drilled hole in the fractured bone, according to an alternate exemplary method of the present invention.
Figure 16:
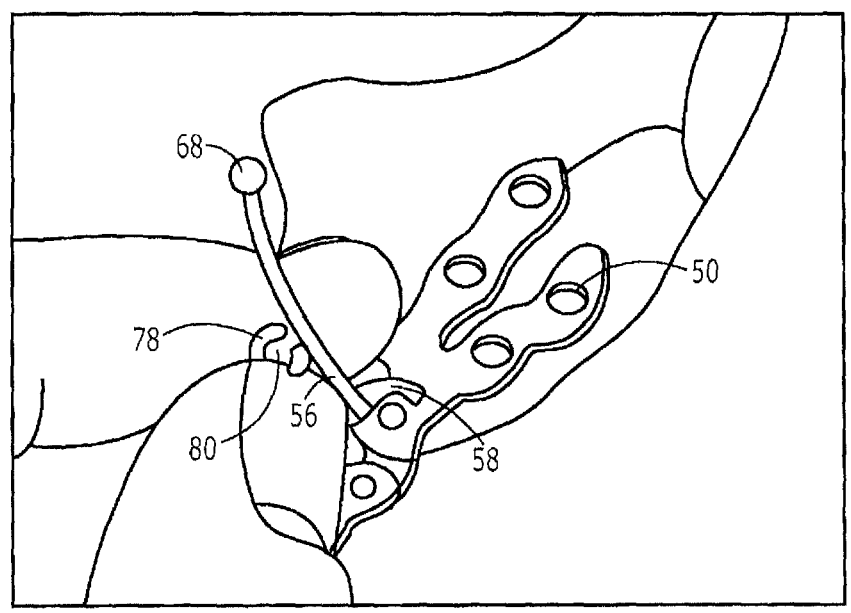
FIG. 16 shows positioning a buttress plate, according to the alternate exemplary method of FIG. 15.
Figure 17:
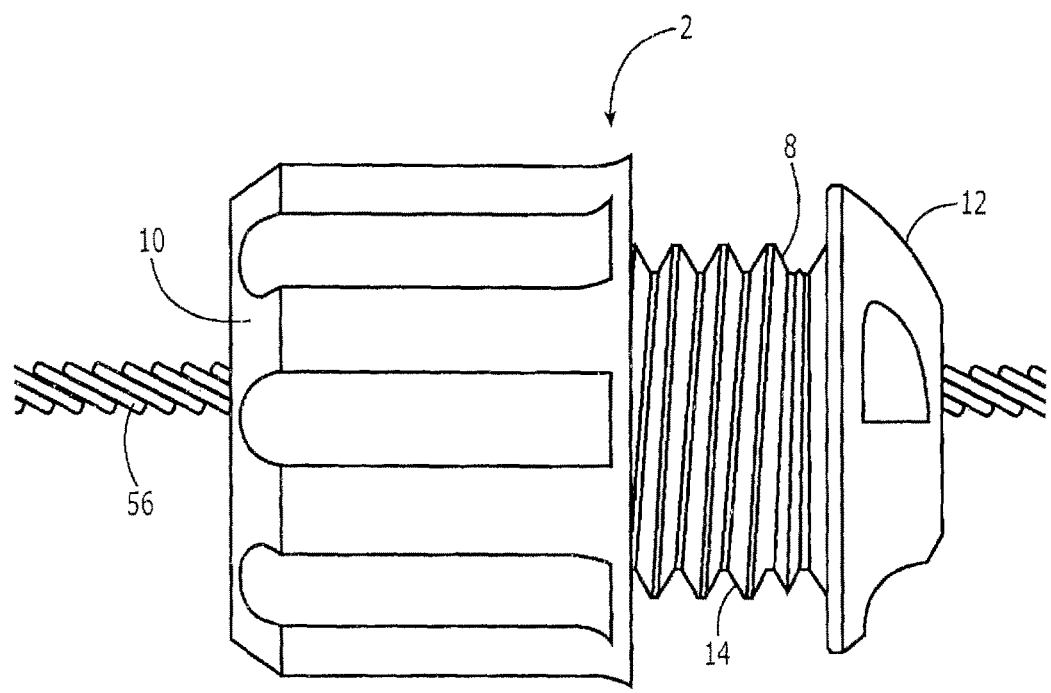
FIG. 17 shows assembling components of an exemplary system, according to an exemplary method of the present invention.
Figure 18:
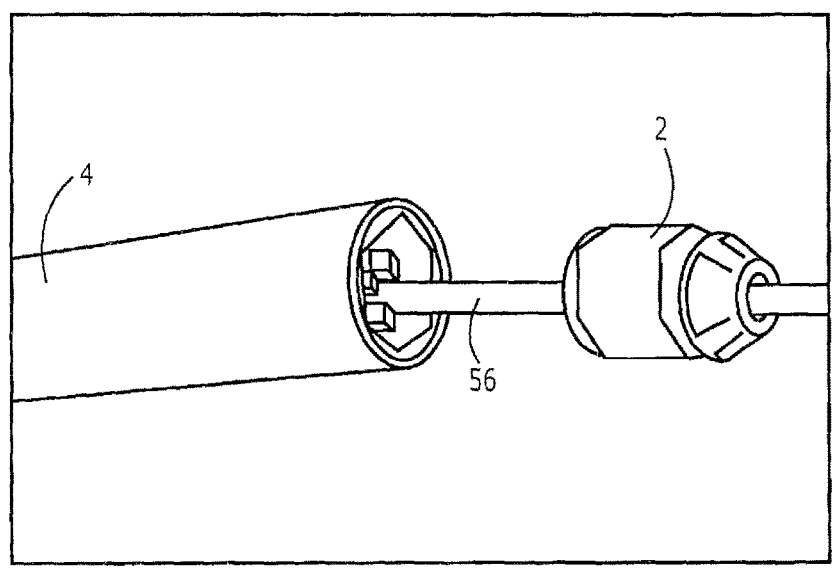
FIG. 18 shows other components of an exemplary system, according to an exemplary method of the present invention.
Figure 19:
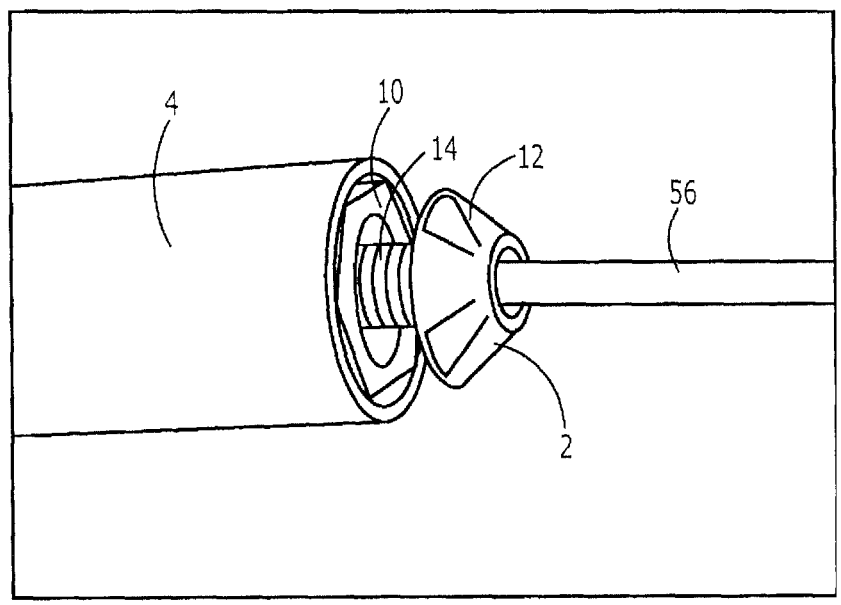
FIG. 19 shows assembled components of an exemplary system, according to an exemplary embodiment of the present invention.

Alternatively, as shown in FIGS. 15 and 16, the cable 56 may be passed through the channel 48 from the dorso-lateral side 46 of the bone 42 such that the distal portion of the cable 56 may extend past the quadrilateral surface. The distal end 68 of the cable 56 may be enlarged, but small enough to pass through the hole 58 of the plate 50 and the channel 48 of the bone 42. Thus, the distal end 68 is passed through the hole 58 and the plate 50 positioned against the quadrilateral surface. It will be understood by those of skill in the art that the plate 50 may have more than one hole 58 such that the distal end 68 of the cable 56 may be inserted through the hole 58 that best positions the plate 50 against the quadrilateral surface. The distal end 68 of the cable 56 may be fixed to the plate 50 via a slotted spherical washer 78, which is affixed to the distal end 68 of the cable 56. The cable 56 is passed through a slot of the slotted spherical washer 78. It will be understood by those of skill in the art that an opening 80 of the spherical washer may be smaller than the distal end 68 such that the distal end 68 may not pass through the opening 80. It will also be understood by those of skill in the art that the spherical washer 78 may be deformed such that a width of the slot is decreased, preventing the cable 56 from coming loose. Thus, when the cable 56 is pulled taught, the plate 50 is held in position against the quadrilateral surface.

Figure 20:
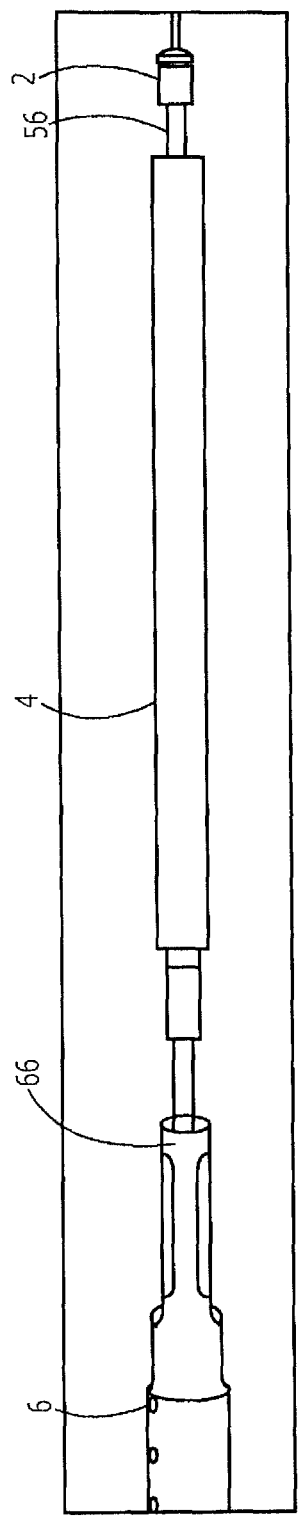
FIG. 20 shows the components of the present invention, fully assembled, according to an exemplary embodiment of the present invention.
Figure 21:
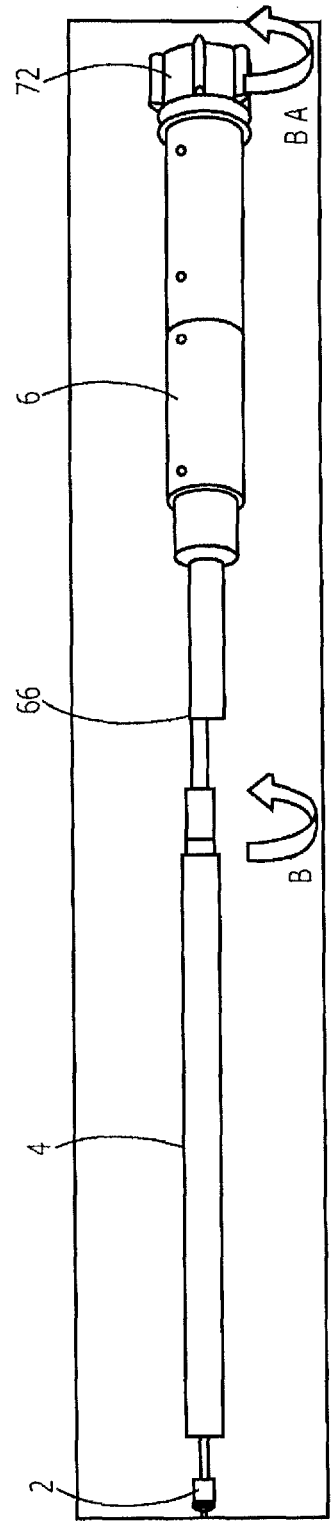
FIG. 21 shows tensioning and crimping a cable, according to an exemplary embodiment of the present invention.

As shown in FIGS. 17-20, while continuing to hold tension on the cable 56, the proximal end thereof is threaded through a clamping mechanism 2, into the inner sleeve 32 and from there into the handle 6 wherein it is engaged with the tensioning mechanism. The proximal end of the clamp 8 is then engaged with the distal end 38 of the inner sleeve 32 while the outer surface 64 of the clamping ring 10 is engaged with the recess 34 at the distal end of the outer sleeve 30 and the entire assembly is slid along the cable 56 until the head 12 of the clamp 8 abuts the dorso-lateral side 46 of the bone 42. The tension through the cable 56 is then increased by actuating the knob 72 of the handle 6 in the direction of arrow A, as shown in FIG. 21. Those skilled in the art will understand that, during this phase, the clamping ring 10 is only screwed over the tapered proximal end of the body 14 so that the portions 62 do not engage the cable 56 and the cable 56 remains slidable through the clamp 8.

It will be understood by those of skill in the art that the clamping mechanism 2 may be clamped over and released from the cable 56 as desired as the clamp 8 may be moveable between a clamping configuration in which the cable 56 is compressed by the radially inward flexing of the portions 62 and a released configuration in which the portions 62 do not compress the cable 56 by biasing the portions 62 toward the released configuration and designing the taper of the portions 62 and the chamfer 30 so that the portions 62 are not plastically deformed when moved to the clamping configuration.

Once the desired tension has been placed on the cable 56, the outer sleeve 30 of the longitudinal member 4 may be rotated in direction B, about the inner sleeve 30, such that the clamping ring 10, to which the outer sleeve 30 is engaged, is screwed over the clamp 8 compressing the portions 62 against the cable 56 and fixing the clamping mechanism 2 on the cable 56 as described above. It will be understood by those in the art that rotating the outer sleeve 30 in one direction relative to the inner sleeve 32 (e.g., direction B) tightens the clamping ring 10 about the body 14 of the clamp 8 while rotating the outer sleeve in the opposite direction loosens the clamping ring 10 from the clamp 8 disengaging the portions 62 from the cable 56.

The clamping mechanism 2, when in the clamped configuration, maintains a desired tension on the cable 56 securing the plate 50 firmly over the quadrilateral surface of the bone 42 while the clamping mechanism 2 is secured firmly against the dorso-lateral side 46 of the bone 42. The head 12 of the clamp 8 abuts and orients to the surface of the bone 42, providing optimal mechanical buttressing. Once the clamping mechanism 2 has been fixed in the clamped configuration, the longitudinal member 4 and the handle 6 may be disassembled, as shown in FIG. 20 by releasing the cable 56 from the tensioning mechanism of the handle 6 and disengaging the distal end 66 of the handle 6 from the proximal end 40 of the inner sleeve 32 of the longitudinal member 4. The handle 6 may then be slid off of the cable 56 and the longitudinal member 4 may then be disengaged from the clamping mechanism 2 by removing the distal end 38 of the inner sleeve 32 from the slots 22 of the clamp 8 and the recess 34 of the outer sleeve 30 from the clamping ring 10. The longitudinal member 4 may then be slid off of the cable 56.

Figure 22:
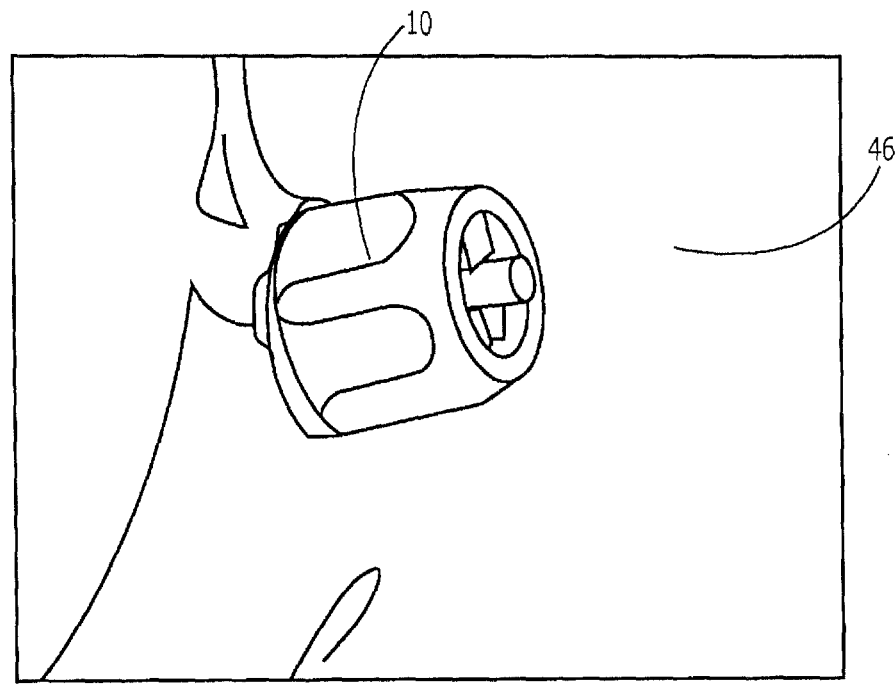
FIG. 22 shows implanted components of an exemplary system, according to an exemplary embodiment of the present invention.
Figure 23:
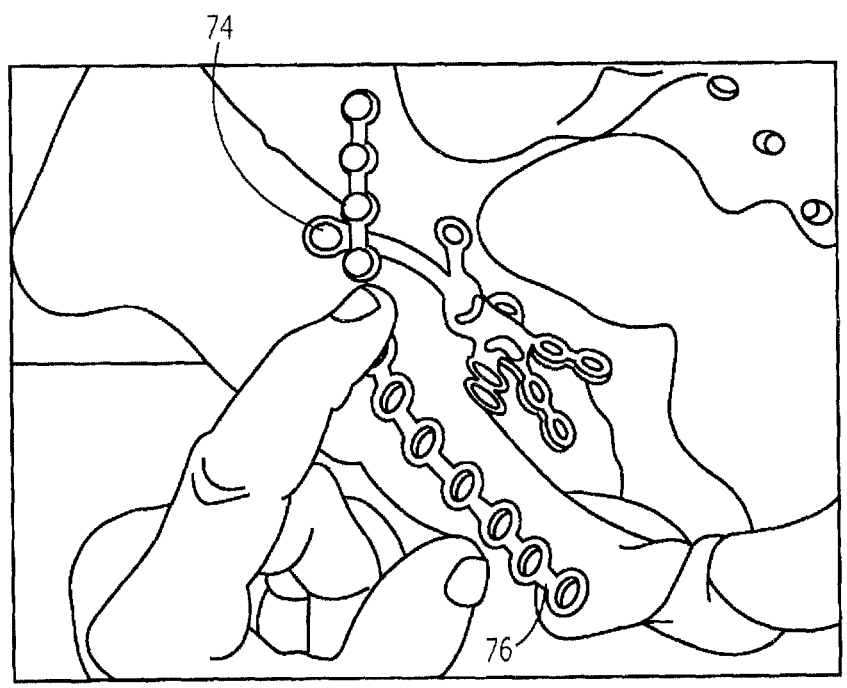
FIG. 23 shows inserting additional screws through a plate, according to an exemplary embodiment of the present invention.

As shown in FIG. 22, the remaining cable 56 may then be cut as close to the clamping mechanism 2 as desired so that only the clamping mechanism 2 remains, projecting out slightly from the dorso-lateral side 46 of the bone 42. As shown in FIG. 23 and as would be understood by those skilled in the art, additional brim screws 74 may be inserted through an additional brim plate 76 to enhance the stability and support of the bone fragments.

As shown in FIGS. 24-29, an alternate embodiment of a clamping mechanism 100 comprises a clamp 102 and a clamping ring 104. The clamping mechanism 100 may be used in the system, as described above, to secure the clamp 102 about the cable 56, at a desired location. The clamp 102 is engagable with the clamping ring 104 to move a mandrel 106 of the clamping ring 104 from a first configuration in which the mandrel 106 permits the cable 56 to slide through the clamping mechanism 100 to a second configuration in which the mandrel 106 crushed against the cable 56 such that the cable 56 is fixed at a desired location.

The clamp 102 includes a head 108 and a body 110 extending distally from a distal end 112 of the head 108 to a distal end 114. The clamp 102 further includes a lumen 116 extending longitudinally therethrough sized to slidably accommodate the cable 56. The head 108 may be sized and shaped to engage a portion of the longitudinal member 4 such that the longitudinal member 4 may move the clamp 102 relative to the clamping ring 104. In a preferred embodiment, the head 108 may be hexagonally shaped to mate with a correspondingly shaped distal end 38 of the inner sleeve 32 of the longitudinal member 4. It will be understood by those of skill in the art that the distal end 38 of the inner sleeve 32 may be a hexagonally shaped recess to accommodate the head 108 of the clamp 102 or any other shaped protrusion or recess so long as the distal end 38 of the inner sleeve 32 mates with the head 108. The body 110 of the clamp 102 may be sized and shaped to engage with the clamping ring 104. The body 110 may include a threading (not shown) about an outer surface 118 thereof. It will be understood by those of skill in the art, however, that the body 108 may include any arrangement or mechanism for engaging with the clamping ring 104. In the embodiment shown, a diameter of the body 110 may be larger than a diameter of the head 108. However, it will be understood by those of skill in the art, that the body 110 may be any size or shape so long as the body 110 is engagable with the clamping ring 104.

As described above, the clamping ring 104 is engagable with at least a portion of the body 110 of the clamp 102 and may be formed as, for example, a nut. The clamping ring 104 includes a channel 120 extending longitudinally therethrough for accommodating the cable 56. The channel 120 may include a first portion 122 and a second portion 124 proximal of the first portion 122. The first portion 122 may be sized and shaped to slidably accommodate the cable 56. Thus, a size of the first portion 122 may be only slightly larger than a size of the cable 56. The second portion 124 may be sized and shaped to accommodate at least a portion of the body 110. Thus, an inner diameter or size of the second portion 124 will be larger than an inner diameter of the first portion 122. The second portion 124 may include a threading (not shown) along an inner surface 126 thereof for rotatably engaging with the threading of the body 110. However, it will be understood by those of skill in the art that the clamping ring 104 may include any mechanism or arrangement for engaging with the clamp 102. An outer surface 128 may be shaped such that the clamping ring 104 may mate with the outer sleeve 30 of the longitudinal member 4. For example, the outer surface 128 may be hexagonally shaped to mate with the hexagonal recess 34 of the outer sleeve 30. Thus, it will be understood by those of skill in the art that when the inner sleeve 32 is rotated relative to the outer sleeve 30, the clamp 102 will rotate relative to the clamping ring 104 such that the clamp 102 engages the clamping ring 104.

Figure 24:
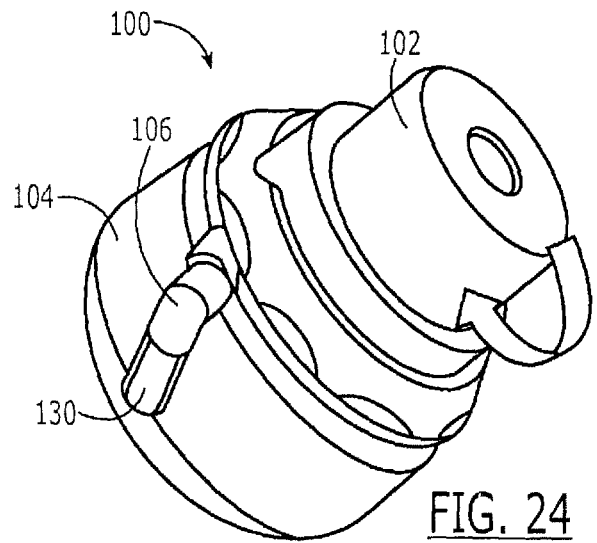
FIG. 24 shows a perspective view of a clamping mechanism according to an alternate embodiment of the present invention, in a first configuration.
Figure 25:
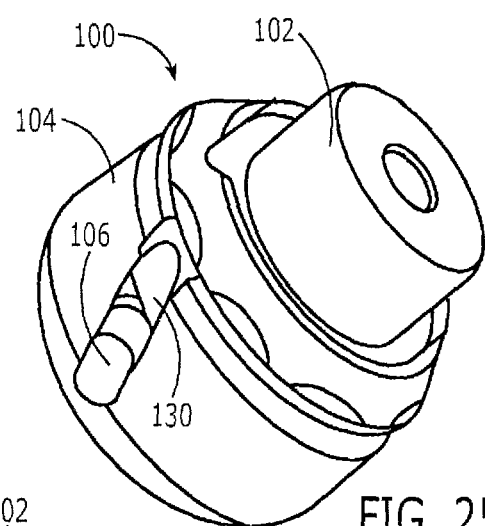
FIG. 25 shows a perspective view of the clamping mechanism of FIG. 24, in a second configuration.
Figure 26:
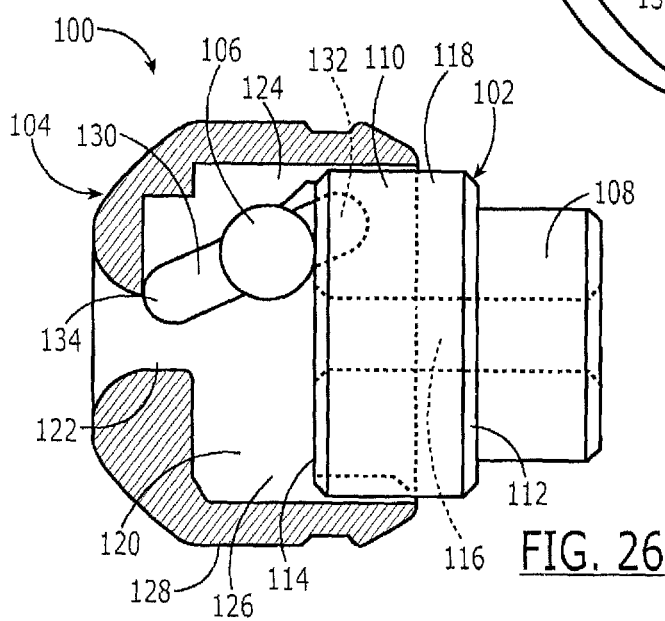
FIG. 26 shows a side view of the clamping mechanism of FIG. 24, in the first configuration.
Figure 27:
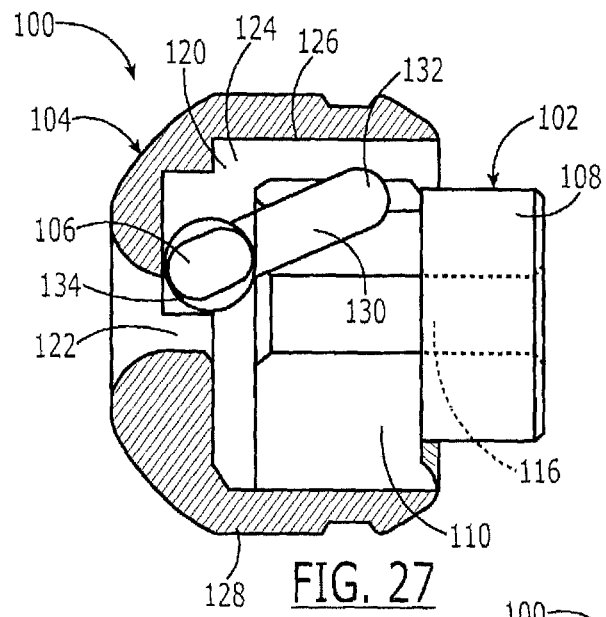
FIG. 27 shows a side view of the clamping mechanism of FIG. 24, in the second configuration.
Figure 28:
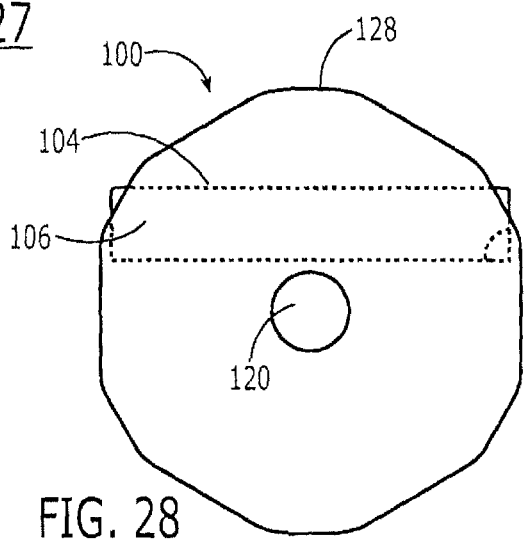
FIG. 28 shows a bottom view of the clamping mechanism of FIG. 24, in the first configuration.
Figure 29:
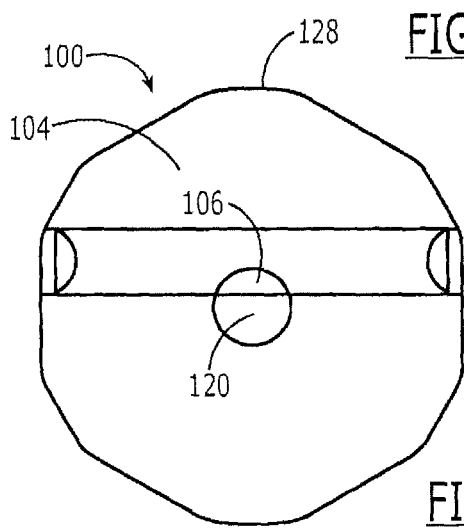
FIG. 29 shows a bottom view of the clamping mechanism of FIG. 24, in the second configuration.

The mandrel 106 may be substantially longitudinally shaped and positioned within the clamping ring 104 such that the mandrel 106 is movable from the first configuration, shown in FIGS. 24, 26 and 28, to the second configuration, shown in FIGS. 25, 27 and 29. The clamping ring 104 includes a slot 130 extending laterally therethrough for accommodating the mandrel 106 such that a length of the mandrel 106 is housed within the channel 120 of the clamping ring 102. The slot 130 is elongated such that a proximal end 132 of the slot 130 accommodates the mandrel 106 in the first configuration while a distal end 134 of the slot 130 accommodated the mandrel 106 in the second configuration. The slot 130 is angled such that the proximal end 132 passes through the second portion 124 of the channel 120 and is radially outward of the first portion 122. Thus, in the first configuration, the mandrel 106 does not interfere with the slidable insertion of the cable 56. The slot 130 angles radially inward from the proximal end 132 toward the distal end 134 such that the distal end 134 is at least partially within the first portion 122, interfering with the channel 120. Thus, the mandrel 106 may slide from the proximal end 132 in the first configuration to the distal end 134 in the second configuration to crush the cable 56 passing through the channel 120, thereby fixing the cable 56.

The mandrel 106 may be moved from the first configuration to the second configuration as the clamp 102 engages the clamping ring 104. The distal end 114 of the clamp 102 abuts the mandrel 106 such that as the clamp 102 is moved relative to the clamping ring 104 to engage with the clamping ring 104, the distal end 114 moves the mandrel 106 distally relative to the clamping ring 104. Thus, the mandrel 106 slides from the proximal end 132 of the slot to the distal end 134 of the slot 130, crushing the cable 56 within the first portion 122 of the channel 120.

It will be apparent to those of skill in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A clamping ring, comprising:
    a body including a channel extending from a body proximal end to a body distal end, the channel including a clamp receiving channel extending from the body proximal end toward the body distal end and a first cable receiving channel extending from the body distal end toward the body proximal end, the clamp receiving channel being coaxial with the first cable receiving channel, the clamp receiving channel shaped and configured to receive a clamp therein such that a second cable receiving channel of the clamp is coaxial with the first cable receiving channel, the first and second cable receiving channels configured to receive a cable drawn to a desired degree of tension by a tensioning mechanism of an actuating mechanism; and
    a mandrel having a length that is slidably housed within the clamp receiving channel along a slot extending laterally through the body, the mandrel configured to move from a first configuration that does not interfere with receiving the cable to a second configuration that crushes the cable from the clamp being received in the clamp receiving channel,
    wherein the body includes a threading that engages a corresponding threading of the clamp such that rotational movement in a clamping direction of the clamp causes the clamp to be received in the clamp receiving channel,
    wherein the clamp is configured to engage a first member of the actuating mechanism that prevents relative movement therebetween, a second member of the actuating mechanism that is movably coupled to the first member engages an outer surface of the body such that rotational movement of the second member in the clamping direction causes the clamp to rotate in the clamping direction so that the body is moved to receive the clamp in the clamp receiving channel.

2. The clamping ring of claim 1, wherein the clamping ring is moveable along a longitudinal axis of the clamp toward a proximal end of the clamp when the clamp is rotated in the clamping direction.

3. The clamping ring of claim 1, wherein the slot is angled radially inward from a first end closer to the body proximal end to a second end closer to the body distal end.

4. The clamping ring of claim 3, wherein the slot is angled such that the second end extends laterally across at least a portion of the first cable receiving channel.

5. The clamping ring of claim 4, wherein, when the mandrel is in the second configuration, the mandrel occupies at least a portion of a cross section of the first cable receiving channel.

6. The clamping ring of claim 1, wherein the mandrel engages a distal end of the clamp such that when the clamp is rotated in the clamping direction, the clamping ring moves toward a proximal end of the clamp and the mandrel moves toward the body distal end.

* * * * *